United States Patent [19]

Tovey et al.

[11] Patent Number: 5,997,858
[45] Date of Patent: Dec. 7, 1999

[54] STIMULATION OF HOST DEFENSE MECHANISMS AGAINST TUMORS

[75] Inventors: Michael Gerard Tovey, Paris, France; Thomas James Kaido, San Diego, Calif.

[73] Assignee: Pharma Pacific Pty Ltd., Brighton-Le-Sands, Australia

[21] Appl. No.: 08/853,293

[22] Filed: May 9, 1997

[30] Foreign Application Priority Data

May 9, 1996 [AU] Australia ................................. PN9765

[51] Int. Cl.$^6$ ..................... A61K 38/21; C07K 14/555; C07K 14/56; C07K 14/57
[52] U.S. Cl. ..................... 424/85.4; 424/85.5; 424/85.6; 424/85.7; 424/1.11; 424/278.1; 514/2; 530/351
[58] Field of Search .................... 424/85.4, 85.5, 424/85.6, 85.7, 1.11, 278.1; 514/2; 530/351

[56] References Cited

U.S. PATENT DOCUMENTS

| | | | |
|---|---|---|---|
| 4,605,555 | 8/1986 | Sato et al. ................................ | 424/85 |
| 5,017,371 | 5/1991 | Cummins ............................... | 424/85.6 |
| 5,019,382 | 5/1991 | Cummins, Jr. .......................... | 424/85.4 |
| 5,286,748 | 2/1994 | Eby, III .................................. | 514/494 |

FOREIGN PATENT DOCUMENTS

| | | |
|---|---|---|
| 0 396 903 | 3/1990 | European Pat. Off. . |
| WO 82/00588 | 4/1982 | WIPO . |
| WO 92/10207 | 6/1992 | WIPO . |

OTHER PUBLICATIONS

Kiskis, J. Interferon Cytokine Res. 15 Supplls 184, 1995 (abstract).

Gutterman, PNAS 91:1198, 1994.

Bocci, Crit Rev. Ther Drug Carrier Syst 9(2):91–133, 1992 (abstract).

Babiuch, Archivum Immunologiae et Therapiae Experimentalis 41(3–4):213–219, 1993 (abstract only).

Caban, Archivom Immunologiae et Therapiae Experimentalis 41(3–4) 1993 pp. 229–235 (abstract only).

Hayden, Frederick G., "Intranasal Interferon α2 for Prevention of Rhinovirus Infection and Illness", The Journal of Infectious Diseases, vol. 148, No. 3 Sep. 1983. pp. 543–550.

Hayden et al., "Human Tolerance Histopathologic Effects of Long Term Administration of Intranasal Interferon–α2", Journal of Infectious Diseases 148:914–921 (1983).

Hayden et al., "Human Nasal Mucosal Responses to Topically Applied Recombinant Leukocyte A Interferon", Journal of Infectious Diseases 156:64–72 (1987).

Machida et al., "Absorption of Recombinant Human Granulocyte Colony–Stimulating Factor (rhG–CSF) from Rat Nasal Mucosa", Pharmaceutical Research 10:1372–1377 (1993).

Samo et al., "Efficacy and Tolerance of Intranasally Applied Recombinant Leukocyte A Interferon in Normal Volunteers", Journal of Infectious Diseases 148:535–542 (1983).

Samo et al., "Intranasally Applied Recombinant Leukocyte A Interferon in Normal Volunteers. II.", Journal of Infectious Diseases 150:181–188 (1984).

Takeda et al., "Pharmacological Activity of Tablets Containing Recombinant Human Granulocyte . . . ", International Journal of Pharmaceutics 101:89–96 (1994).

Watanabe et al., "Absorption and Blood Leukocyte Dynamics of Recombinant Human Granulocyte Colony–Stimulating Factor . . . ", International Journal of Pharmaceutics 110:93–97 (1994).

Primary Examiner—Nancy A Johnson
Attorney, Agent, or Firm—Heller Ehrman White & McAuliffe

[57] ABSTRACT

A method for treating neoplastic disease in a mammal via administering to the mammal a therapeutically effective amount of an interferon via oromucosal contact. The amount of interferon administered is less than an amount which induces a pathological response when administered parenterally.

16 Claims, No Drawings

STIMULATION OF HOST DEFENSE MECHANISMS AGAINST TUMORS

This invention relates to methods of stimulation of host defense mechanisms against pathological conditions in a host mammal by administration of interferon via the oromucosa. In particular, the invention is applicable to methods of treatment of neoplastic diseases.

BACKGROUND OF THE INVENTION

Alpha interferons are used widely for the treatment of a variety of hematological malignancies including hairy cell leukemia, chronic myelogenous leukemia, low grade lymphomas, cutaneous T-cell lymphomas, and solid tumors such as renal cell carcinoma, melanoma, carcinoid tumors and AIDS-related Kaposi's sarcoma (Gutterman, J. U., *Proc. Natl. Acad Sci. USA,* 1994 91: 1198–1205). Antitumor effects are usually seen at high dosage levels, often of the order of tens of millions of units of interferon-α (IFN-α), administered by parenteral injection. Interferon-α is a Type I interferon, a class which also includes the β and ω interferons. Although a number of routes of administration, including intravenous, subcutaneous, intramuscular, topical, and intralesional injection, are commonly employed for the administration of type I interferons, the oral route has not been generally used, because interferons are proteins which are considered to be inactivated by proteolytic enzymes and which are not absorbed appreciably in their native form in the gastrointestinal tract. Indeed a number of studies have failed to detect interferons in the blood following oral administration (Cantell and Pyhäla, *J. Gen. Virol.,* 1973 20: 97–104; Wills et al, *J. IFN Res.,* 1984 4: 399–409; Gilson et al, *J. IFN Res.,* 1985 5: 403–408).

There have been a number of anecdotal reports of efficacy of low doses of interferon administered as a nasal spray or as an oral liquid formulation in the treatment of a variety of conditions, particularly influenza. A series of patent specifications has described the use of low doses of orally administered interferon of heterologous species origin for the treatment of infectious rhinotracheitis ("shipping fever") in cattle, and of feline leukemia, and also treatment of other conditions, for enhancement of efficiency of vaccines; for improving the efficiency of food utilization; and for prevention of bovine theileriosis. See U.S. Pat. No. 4,462,985, Australian Patent No. 608519, Australian Patent No. 583332 and U.S. Pat. No. 5,215,741 respectively. In addition U.S. Pat. No. 5,017,371 discloses the use of interferon in this way for treatment of side-effects of cancer chemotherapy or radiotherapy. In these specifications, the interferon used was human interferon-α prepared by the method of Cantell, administered in phosphate buffered saline, at a dose of 0.01 to 5 IU per pound body weight. While these specifications suggest that such low doses of interferon administered to the oropharyngeal mucosa, preferably in a form adapted for prolonged contact with the oral mucosa, may be efficacious for treatment of a wide variety of conditions including cancer, the experimental evidence for conditions other than shipping fever, feline leukemia, canine parvovirns and theileriosis is largely anecdotal. In particular, no properly controlled trials of this treatment in any animal model for human cancers are presented.

In contrast, the invention disclosed herein is based upon the first controlled study in an animal model of the efficacy of oromucosally administered interferon for the treatment of neoplastic diseases.

SUMMARY OF THE INVENTION

This invention provides a method for treating neoplastic disease in a mammal via administering to the mammal a therapeutically effective amount of an interferon via oromucosal contact. The amount of interferon administered is less than an amount which induces a pathological response when administered parenterally. In particular, the invention provides a method for treating multiple myeloma, hairy cell leukemia, chronic myelogenous leukemia, low grade lymphoma, cutaneous T-cell lymphoma, carcinoid tumors, cervical cancer, sarcomas including Kaposi's sarcoma, kidney tumors, carcinomas including renal cell carcinoma, hepatic cellular carcinoma, nasopharyngeal carcinoma, hematological malignancies, colorectal cancer, glioblastoma, laryngeal papillomas, lung cancer, colon cancer, malignant melanoma, and brain tumors including malignant brain tumors. In one embodiment, the method is generally applicable in the treatment of tumors of non-viral etiology.

The oromucosal administration may involve administering an effective dose of interferon in a single dose or the effective dose may be administered in a plurality of smaller doses over a period of time sufficient to elicit host defense stimulation equivalent to that of a single dose. Likewise, the effective dose of interferon may be administered continuously over a period of time sufficient to elicit host defense stimulation equivalent to that of a single dose.

The method may be practiced by administering from about 1500, preferably from about 5000 IU, to about $20 \times 10^6$ IU of interferon, more preferably from about $1 \times 10^4$ IU to about $20 \times 10^6$ IU of interferon, most preferably from about $1 \times 10^4$ to about $1 \times 10^6$ IU of interferon, provided that the chosen dose is one which is less than the amount which induces a pathological response when administered parenterally. These dose ranges generally refer to homologous interferon α in man. For other types of interferon the dose that will induce a pathological response may differ from that induced by homologous interferon α in man. A physician treating a patient with a particular type of interferon will be able to readily identify the suitable dose range for the patient to be treated.

In another embodiment, the invention provides a pharmaceutical composition for oromucosal administration comprising a therapeutically effective amount of at least one interferon. The composition may be provided as a solution, tablet, lozenge, gel, syrup, paste, or controlled release oromucosal delivery system. Optionally, the composition may contain buffers, stabilizers, thickening agents, absorption, and viscosity enhancers, and the like.

In one embodiment, the pharmaceutical composition is provided in unit dosage form having from about from about 1500 IU, preferably 5000 IU, to about $20 \times 10^6$ ;U of interferon, more preferably from about $1 \times 10^4$ ;U to about $20 \times 10^6$ IU of interferon, most preferably from about $1 \times 10^4$ to about $1 \times 10^6$ IU of interferon.

The method may be practiced either as the sole therapeutic approach, or as an adjunct to chemo or radiation therapy, or with other cytokines, such as interleukin-2, 12, or 15, or with IFN-inducers.

The method is conducted using a Type I or II interferon, selected from α, β, γ, ω, and consensus interferons, most preferably with a recombinant IFN-α.

DETAILED DESCRIPTION OF THE INVENTION

The invention will now be described in detail by way of reference only using the following definitions and examples. All patents and publications referred to herein are expressly incorporated by reference.

Definitions

As used herein, "interferon" refers to a Type I or Type II interferon, including those commonly designated as α, β, γ, and ω, and mixtures thereof, including the consensus sequence. Interferons are available from a wide variety of commercial sources and are approved for the treatment of numerous indications. The interferon may be from natural sources, but is preferably a recombinant product. For the purposes of the invention, the term "interferon" also includes polypeptide fragments which have interferon activity, and chimeric or mutant forms of interferon in which sequence modifications have been introduced, for example to enhance stability, without affecting the nature of their biological activity, such as disclosed in U.S. Pat. Nos. 5,582,824, 5,593,667, and 5,594,107 among others.

Optionally the interferon may be administered concurrently with an inducer of interferon synthesis and release. The inducer may be administered together with the interferon, or may be administered separately. Inducers of interferon include, for example, polynucleotides such as poly I:C; preferably a low molecular weight, orally administrable interferon inducer is used. Suitable inducers are known in the art for example, Tilorone (U.S. Pat. No. 3592819; Albrecht et al, *J. Med. Chem.* 1974 17: 1150–1156) and the quinolone derivative Imiquimod (Savage et al; *Brit. J. Cancer,* 1996 74: 1482–1486).

The methods and compositions of the invention may optionally be used in conjunction with one or more other treatments for the specific condition, and the attending physician or veterinarian will readily be able to select such other treatment as may be appropriate in the circumstances.

In one embodiment, the invention provides a method of treatment of a neoplastic condition in a mammal, comprising the step of administering interferon as described above. The neoplastic condition may be metastatic cancer.

While the method of the invention may be used without concurrent treatment with other agents, it is contemplated that this embodiment of the invention will be particularly useful in the following settings:

a) as adjuvant therapy, subsequent to surgery, chemotherapy, or radiotherapy given by standard protocols;

b) for treatment of interferon-sensitive neoplasias, the method of the invention is utilized either alone or in conjunction with conventional chemotherapy or radiotherapy; and c) for treatment of interferon-resistant neoplasias, the method of the invention is utilized either alone or most preferably in conjunction with conventional chemotherapy or radiotherapy.

The above methods are directed at inducing and/or maintaining remission of disease. By "in conjunction with other treatment" is meant that the interferon is administered before, during and/or after the radiotherapy or other chemotherapy. The most suitable protocol will depend on a variety of factors, as discussed below.

In particular, it is contemplated that the method of the invention will preferably be used in conjunction with at least one other treatment selected from the group consisting of chemotherapy using cytostatic drugs, one or more other cytokines which have anti-cancer activity but which have a different mechanism of action from that of interferon, anti-angiogenic agents, and agents which potentiate the activity of interferon. Preferably the second cytokine is interleukin-1 (IL-1), interleukin-2 (IL-2) interleukin-12 (IL-12), or interleukin-15 (IL-15); preferably the angiogenesis inhibitor is AGM-1470 [(Chloroacetyl)-carbamic acid (3R-(3α, 4α (2R*, 3R*), 5β, 6β))-5-methoxy-4-(2-methyl-3-(3-methoxy-2-butenyl)oxiranyl)-1-oxaspiro(2.5)oct-6-yl ester]; preferably the interferon-potentiating treatment is hyperthermia or arginine butyrate.

Preferred cytostatic drugs to be administered in conjunction with interferon include but are not limited to cyclophosphamide, cisplatin, carboplatin, carmustine (BCNU; N,N-Bis(2-chloroethyl)-N-nitrosourea), methotrexate, adriamycin, α-difluoromethylornithine, and 5-fluorouracil.

The neoplastic conditions susceptible to this method include but are not limited to cancers which respond to parenteral administration of high doses of IFN-α, such as hematological malignancies, e.g. multiple myeloma, hairy cell leukemia, or chronic myelogenous leukemia, low grade lymphomas, solid tumors such as renal cell carcinoma and melanoma, or carcinoid tumors, in particular tumors of non-viral etiology.

In the preparation of the pharmaceutical compositions of this invention, a variety of vehicles and excipients for IFN may be used, as will be apparent to the skilled artisan. Representative formulation technology is taught in, inter alia, Remington: The Science and Practice of Pharmacy, 19th ed., Mack Publishing Co., Easton, Pa., 1995, and its predecessor editions. The IFN formulation may comprise stability enhancers, such as glycine or alanine, as described in U.S. Pat. No. 4,496,537, and/or one or more carriers, such as a carrier protein. For example, for treatment of humans pharmaceutical grade human serum albumin, optionally together with phosphate-buffered saline as diluent, is commonly used. Where the excipient for IFN is human serum albumin, the human serum albumin may be derived from human serum, or may be of recombinant origin. Normally when serum albumin is used it will be of homologous origin.

The IFN may be administered by any means which provides contact of the IFN with the oromucosal cavity of the recipient. Thus it will be clearly understood that the invention is not limited to any particular type of formulation. The present specification describes administration of IFN deep into the oromucosal cavity; this may be achieved with liquids, solids, or aerosols, as well as nasal drops or sprays. Thus the invention includes, but is not limited to, liquid, spray, syrup, lozenges, buccal tablets, and nebuliser formulations. A person skilled in the art will recognize that for aerosol or nebuliser formulations the particle size of the preparation may be important, and will be aware of suitable methods by which particle size may be modified.

In one aspect, the interferon is administered in a single daily dose. Alternatively, the interferon is administered in a plurality of lower doses, distributed over time, so that the net effect is equivalent to the administration of the single higher dose. One approach to this delivery mode is via the provision of a sustained or controlled release device adhered to or implanted in the oromucosal cavity and designed to release interferon over time in an amount equivalent to a single high dose.

Representative formulations of interferon for oromucosal use include the following (all % are w/w):

Tablet: Dextrose BP 45%; gelatin BP 30%; wheat starch BP 11%; carmellose sodium BP 5%; egg albumin BPC 4%; leucine USP 3%; propylene glycol BP 2%; and $1 \times 10^6$ IU IFN-α2. The tablet may be used as is and allowed to slowly dissolve in the mouth or may be dissolved in water and held in the mouth in contact with the oromucosa as needed.

An interferon paste may be prepared, as described in U.S. Pat. No. 4,675,184, from glycerin 45%, sodium CMC 2%, citrate buffer (pH 4.5) 25%, distilled water to 100%, and $1\times10^6$ IU IFN.-α2 The interferon paste may be adhered to the buccal mucosa.

Likewise, a gargle or a syrup may be prepared by adding the desired amount of interferon to a commercially available mouthwash or cough syrup formulation.

Within the specific dose ranges referred to above, the optimal treatment in any individual case will depend on the nature of the condition concerned, the stage of disease, previous therapy, other continuing therapy, the general state of health of the mammal, the sensitivity of the subject to interferon, etc., and therefore will be at the physician's or veterinarian's discretion, bearing in mind all these circumstances. The length of treatment will of course vary with the condition being treated, for example, treatment of a slow-growing cancer, such as prostate cancer, would be expected to involve a different course of treatment than treatment of a rapidly growing cancer, such as hepatic cellular carcinoma.

The effective dose disclosed herein is one which has an anti-tumor effect when administered oromucosally and does not generate a pathological response in the mammal when administered parenterally. A pathological response may be acute, chronic, or cumulative, and may be manifested by changes in blood chemistry, such as leukopenia, bone marrow depression, or other histological parameters. As used herein, a pathological response includes adverse side effects, such as fever, malaise, or flu-like symptoms, vascular reactions, such as phlebitis, and local inflammatory reactions at the site of injection. Such responses will vary considerably among the patient population in view of individual variations in sensitivity to interferon. A simple test for identifying an acceptable low dose of interferon for oromucosal therapy is to inject the patient with the putative acceptable dose, based upon considerations of age, weight, indication, progression, etc. and ascertain if the injection produces a pathological response as defined herein, with local irritation at the site of injection being the most readily ascertainable criterion. If no adverse response is noted, then the same dose may be administered oromucosally. If there is an undesirable response, then the process is repeated at a lower dose, until a non-pathological dose is identified. Oromucosal administration provides increased ease of administration and decreased risk of infection.

For many patients, it is expected that oromucosal doses will be approximately the same as those known to be well tolerated and effective in existing approved parenteral protocols. Therefore, for purposes of specificity, an acceptable low dose of interferon may be from about 1500 IU, preferably from about 5000 IU, to about $20\times10^6$ IU of interferon per day. More preferably the dose is from about $1\times10^4$ IU to about $20\times10^6$ IU of interferon per day, most preferably from about $1\times10^4$ IU to about $1\times10^6$ IU of interferon per day, provided that the dose is one which does not induce a pathological response when administered parenterally. In one embodiment, the total dose may be administered in multiple lower doses over time, or even may be delivered continuously or in a pulsatile manner from a controlled release device adhered to or implanted in the oromucosa.

INTERFERONS AND INTERFERON FORMULATIONS

Mouse IFN-α/β

Mouse IFN-α/β (Mu IFN-α/β) was prepared from cultures of C243-3 cells induced with Newcastle disease virus (NDV) and purified as described previously (Tovey et al, Proc. Soc. Exp. Biol. and Med., 1974 146: 809–815). The preparation used in this study had a titer of $4\times10^6$ International Units (IU)/ml and a specific activity of $5\times10^7$ IU/mg protein as assayed on mouse 929 cells challenged with vesicular stomatitis virus (VSV) as described previously (Tovey et al, Proc. Soc. Exp. Biol. and Med., 1974 146: 809–815). The preparation was standardized against the international reference preparation of murine IFN-α/β of the National Institutes of Health (NIH) (G-002-9004-5411).

Human IFN-α-1-8

Recombinant human IFN-α 1–8 (Hu IFN-α 1–8; BDBB lot no. CGP 35269-1, Ciba-Geigy, Basel, Switzerland) was prepared and purified as described previously (Meister et al, J. Gen. Virol., 1986 67:1633–1643). The preparation used in this study had a titer of $70\times10^6$ IU/ml on homologous human WISH cells challenged with VSV as described previously (Tovey et al, Nature, 1977 267: 455–457), and a titer on heterologous mouse L929 cells of $1\times10^6$ IU/ml. The preparation was standardized against both the NIH human IFN-α international reference preparation (G-023-901-527) and the NIH murine IFN-α/β standard (G-002-9004-5411). The specific activity of the IFN preparation was $2\times10^8$ IU/mg protein.

RECOMBINANT MURINE INTERFERON-α

Recombinant murine interferon-α was purchased from Life Technologies Inc. The preparation used in this study (lot no. HKK404) had a titer of $6\times10^6$ IU/mi and a specific activity of $6\times10^8$ IU/mg protein as assayed on mouse L929 cells challenged with VSV (Tovey et al, Proc. Soc. Exp. Biol. Med., 1974, 146:406–415).

RECOMBINANT MURINE INTERFERON β

Recombinant murine interferon β was purchased from R & D Systems Inc. The preparation used in this study (lot no. 1976-01S) had a titer of $3.2\times10^4$ IU/ml and a specific activity of $8\times10^6$ IU/mg protein as assayed on mouse L929 cells challenged with VSV (Tovey et al, proc. Soc. Exp. Biol. Med., 1974, 146:406–415).

RECOMBINANT MURINE INTERFERON γ

Recombinant murine interferon γ was purchased from R & D Systems Inc. The preparation used in this study (2580-03SA) had a titer of $2\times10^5$ IV/ml and a specific activity of $1\times10^7$ IU/mg protein as assayed on mouse L929 cells challenged with VSV (Tovey et al, Proc. Soc. Exp. Biol. Med., 1974, 146:406–415).

All the interferon preparations were titrated simultaneously in the same assay and standardized against the international reference preparation of murine interferon α/β of the US National Institutes of Health (G-002-9004-5411).

EXCIPIENT

Interferon preparations were diluted in phosphate buffered saline (PBS) containing bovine serum albumin (BSA) or in a proprietary excipient. Bovine serum albumin fraction V (RIA grade; immunoglobulin free; Cat. no. A7888; Sigmia; USA) was dissolved at a final concentration of 100 μg/ml in PBS (pH 7.4) and sterilized by filtration (0.2μ, Millex-GV, Millipore, USA).

The proprietary excipient used was as follows, supplied in the form of tablets (Ferimmune™, Pharma Pacific):

|  | % w/w | mg/tablet |
|---|---|---|
| Dextrose (Glucose) BP** | 44.67*** | 55.84 |
| Gelatin BP** | 30.06 | 37.58 |
| Wheat Starch BP** | 11.31 | 14.14 |
| Carmellose Sodium BP** | 4.96 | 6.20 |
| Egg Albumen BPC** | 4.03 | 5.04 |
| Leucine USP | 3.00 | 3.75 |
| Propylene Glycol BP | 1.88 | 2.35 |
| Dextran 40** (as Dextran 40 Injection BP) | 0.06 | 0.08 |
| Sodium Phosphate BP | 0.03 | 0.04 |
| Sodium Chloride BP | 0.01 | 0.01 |
| Sodium Acid Phosphate BP | 0.01 | 0.01 |
| Total | 100.02 | 125.04 |

**Calculated on an anhydrous basis
***Derived from:
Dextrose (Glucose) BP (anhydrous) 44.64%
Glucose BP (as Dextran 40 Injection BP) 0.03%

A single tablet was dissolved in 1.5 ml phosphate buffered saline, centrifuged at 16,000 g for 15 ml, and then sterile filtered (0.2$\mu$, Millex-GV, Millipore, USA), and stored at 4° C. prior to use. Excipient was prepared daily prior to use.

INTERFERON DELIVERY SYSTEM

Preliminary experiments showed that the application of 5 $\mu$l of crystal violet to each nostril of a normal adult mouse using a P20 Eppendorf micropipette resulted in an almost immediate distribution of the dye over the whole surface of the oropharyngeal cavity. Staining of the oropharyngeal cavity was still apparent some 30 minutes after application of the dye. Essentially similar results were obtained using $^{125}$I-labeled recombinant human IFN-$\alpha$ 1–8 applied in the same manner. This method of administration was therefore used in all subsequent experiments.

For the purposes of the animal experiments described in this specification, it will be clearly understood that the expressions "oromucosal" or "oropharyngeal" or "intranasal/oral" or "intranasal plus oral" or "in/or" with reference to the route of administration of IFN is to be taken to mean administration of the IFN preparation deep into the nasal cavity so that it is rapidly distributed into the oromucosal cavity, i.e. the mouth and throat of the recipient mammal, so as to make contact with the mucosa lining this cavity.

FRIEND ERYTHROLEUKAEMIA CELLS

The IFN-$\alpha$/$\beta$ resistant clone, 3C18, of Friend erythroleukaemia cells (FLC) was obtained from Dr E. Affabris, Rome and is described in detail by Affabris et al, 1982 (*Virology*, 120: 441–452). These cells were subsequently maintained by in vivo passage. Briefly, DBA/2 mice were inoculated by intraperitoneal injection (ip) with approximately 100 LD$_{50}$ of 3C18 cells and one week later the tumor cells were harvested from the peritoneum of the mice, counted and other mice were again inoculated with 100 LD$_{50}$ of 3C18 cells. This procedure was repeated for 60 to 100 passages. It has been shown that the 3C18 cells used at the 60th to 100th in vivo passage are highly metastatic for the liver and spleen (Gresser et al, *Int. J. Cancer*, 1987 39: 789–792). The phenotype of IFN resistance was confirmed routinely by cultivating the in vivo passaged cells in vitro in the presence of IFN-$\alpha$/$\beta$ (Belardelli et al, *Int. J. Cancer*, 1982 30: 813–820).

ANIMALS

The mice used in this study were obtained from a specific pathogen-free colony (IFFA CREDO, France). They were housed in a specific pathogen-free animal facility at the Institut Federatif CNRS at Villejuif according to EEC standards.

INTERFERON BIOASSAY

Interferon was assayed according to a conventional method. Briefly, samples (20 $\mu$l) were diluted in 80 $\mu$l of Eagle's Minimal Essential Medium (MEM) (Gibco, France) containing 2% heat-inactivated Fetal Calf Serum (FCS) (Gibco, France) and added to each well of a microtitre plate (Falcon, cat. no. 3072) using a multichannel micro-pipette (Finnpipette, Labsystem, 50-300 T1). WISH or L929 cells (2×10$^4$ cells/well) were added in 100 $\mu$l of MEM containing 2% FCS and incubated overnight at 37° C. in an atmosphere of 5% $CO_2$ in air (Forma 3029 $CO_2$ incubator). The cells were then examined for any signs of toxicity using an Olympus IM GLDW inverted microscope equipped with a 10× objective. Samples which did not exhibit detectable toxicity were then subjected to serial two-fold dilutions starting from an initial 1: 10 dilution in a total volume of 200 $\mu$l of Eagle's MEM containing 2% FCS, by carrying forward 100 $\mu$l of diluted material with a multichannel micropipette, in a microplate containing 100 $\mu$l per well of fresh Eagle's MEM containing 2% FCS, Appropriate serial two-fold dilutions of the NIH human IFN-$\alpha$ reference standard (G-023-901-527) or the NIH Mu IFN-$\alpha$/$\beta$ reference standard (G-002-9004-5411) were also prepared. WISH or L929 cells (2×10$^4$ cells/well) in 100 $\mu$l of Eagle's MEM containing 2% FCS were then added to each plate where appropriate and incubated overnight at 37° C. in an atmosphere of 5% $CO_2$ in air. The cell monolayers were then checked for any signs of toxicity and in the absence of any apparent toxicity, the culture was aspirated and replaced with 200 $\mu$l of Eagle's MEM containing 2% FCS containing 100 TCID$_{50}$ of VSV (2×10$^{-4}$ VSV$_{23}$ for WISH cells, or 10$^{-5}$ VSV$_{23}$ for L929 cells). The plates were then incubated overnight at 37° C. in an atmosphere of 5% $CO_2$ in air. The cell monolayers were then examined for specific viral cytopathic effect using an Olympus IM ULWD inverted microscope. Interferon titers were determined from the reciprocal of the dilution which gave 50% protection against specific viral cytopathic effect, and are expressed in international reference units/ml (IU/ml).

EXAMPLE 1

Anti-Tumor Activity of Oromucosally Administered Interferon-$\alpha$ in Mice Challenged with Friend Erythroleukaemia Cells In order to establish whether IFN-$\alpha$ administered by the intranasal/oral (in/or) route increases the survival of mice challenged with highly metastatic FLC cells, groups of six 7–8 week-old male DBA/2 mice were challenged intravenously (iv) with 1×10$^5$ FLC on day 0.

Each group of mice was treated twice a day for 10 consecutive days by the in/or route with either 10$^4$ IU of a natural mixture of multiple murine IFN-$\alpha$ subtypes (Mu IFN-$\alpha$) in 10 $\mu$l BSA-PBS, or with an equal volume of a mock IFN preparation, which was produced and purified in the same manner as the IFN preparation with the exception of the omission of the virus inducer. The mock IFN preparation did not exhibit detectable IFN activity when assayed in parallel with the purified Mu IFN-$\alpha$ preparation. The results are shown in Table 1.

TABLE 1

| Group | Treatment | Day of Death | Mean day of death ± SE |
|---|---|---|---|
| 1 | Mock Mu IFN-α | 9,9,10,10,10,10 | 9.6 ± 0.2 |
| 2 | Mu IFN-α10$^4$ IU | 28,31,36>100>100 | 31.7 ± 2.3** |

**Calculated for dead animals only

Oromucosal administration of $10^4$ IU of Mu IFN-α twice a day dramatically increased the survival time of mice injected with FLC. In fact 2 of 5 mice were effectively cured as they were alive and well 100 days after challenge with $2 \times 10^4$ LD$_{50}$ of FLC, despite cessation of IFN-α treatment after only 20 days. The results of controlled tests on groups of 10 adult DBA/2 mice infected with $2 \times 10^4$ LD$_{50}$ of FLC and treated oromucosally with $10^3$ IU of recombinant murine IFN-β or $10^3$ IU of recombinant murine IFN-γ were similar.

EXAMPLE 2

Larger Trial of Anti-Tumor Activity of Low Dose Oromucosal Interferon-α in Mice Injected with Friend Erythroleukaemia Cells In order to confirm the results of Example 1, a larger trial was performed. One hundred fifty 8 week-old female DBA/2 mice were challenged iv with $1 \times 10^3$ FLC ($2 \times 10^4$ FLC LD$_{50}$) on day 0. Mice were treated with the type and dose of IFN indicated, administered by the in/or route in a 10 μl volume twice a day for 10 consecutive days. These were 10 mice in each treatment group. The results are summarized in Table 2.

TABLE 2

| Group | Treatment | Dose | Excipient | Mean day of death ± SE |
|---|---|---|---|---|
| 1 | None | — | None | 9.5 ± 0.2 |
| 2 | Mock Mu IFN-α | — | BSA/PBS | 9.6 ± 0.2 |
| 3 | Mu IFN-α | $10^4$ IU | BSA/PBS | 29.4 ± 25.6%* |
| 4 | Mu IFN-α | $10^3$ IU | BSA/PBS | 11.6 ± O.2 |
| 5 | Mu IFN-α | $10^2$ IU | BSA/PBS | 10.3 ± O.2 |
| 6 | Hu IFN-α 1–8 | $10^4$ IU | BSA/PBS | 18.2 ± O.8 |
| 7 | Hu IFN-α 1–8 | $10^3$ IU | BSA/PBS | 13.1 ± 0.8 |
| 8 | HU IFN-α 1–8 | $10^2$ IU | BSA/PBS | 11.4 ± 0.5 |

IU: International reference units
BSA/PBS: 100 μg/ml of BSA in PBS pH 7.4
Mu IFN-α: natural mixture of murine IFN-α subtypes
Hu IFN-α: single recombinant human IFN-α isotype
*: Some of the animals in this group were still alive at 100 days post treatment IFN-α administered by the in/or route exhibits a marked anti-tumor activity in mice challenged iv with FLC. Indeed, some IFN-treated mice can be considered to be cured, as they were still alive more than 100 days after inoculation of 100,000 FLC, in a system in which 4 to 5 FLC cells are sufficient to kill an animal.

Pure preparations of a single recombinant IFN-α subspecies, IFN-α 1–8, a natural mixture of multiple IFN-α subtypes, Mu IFN-α, recombinant murine IFN-β, and recombinant murine IFN-γ exhibit marked anti-tumor activity in this model when administered by the in/or route, strongly suggesting that the observed anti-tumor activity of oromucosally administered IFN preparations is indeed due to the IFN component of these preparations.

EXAMPLE 3

Effect of Route of Administration of Interferon on Anti-Tumor Activity

The effect of in/or administered IFN was compared with that of IFN given by conventional routes. Eight week-old female DBA/2 mice were challenged iv with $1 \times 10^5$ FLC ($2 \times 10^4$ FLC LD$_{50}$) on day 0. Mice were treated twice a day for 10 consecutive days with $10^4$ IU of Mu IFN-α (the optimal dose as determined in Example 2) administered by the route indicated. There were 6 mice in each treatment group, and in each case the excipient for the Mu IFN-α was BSA in PBS. The results are summarized in Table 3.

| Group | Treatment | Route | Mean day of death ± SE |
|---|---|---|---|
| 1 | None | | 9.6 ± O.2 |
| 2 | Mu IFN-α | Intranasal/oral | 30 ± 25.85%* |
| 3 | Mu IFN-α | Oral | 18.5 ± 2.0 |
| 4 | Mu IFN-α | Gastric | 13.5 ± 1.3 |
| 5 | Mu IFN-α | Subcutaneous | 23.5 ± 1.6 |
| 6 | Mu IFN-α | Intramuscular | 23.7 ± 1.8 |
| 7 | Mu IFN-α | Intravenous | 25.0 ± 1.2 |
| 8 | Mu IFN-α | Intraperitoneal | 26.7 ± 4.1 |

IU: international reference units
BSA/PBS: 100 μg/ml of BSA in PBS pH 7.4
*: Some of the animals in this group were still alive 100 days after inoculation of FLC cells.

The oromucosal (or in/or) route of administration is at least as effective as the commonly used parenteral routes, such as iv, intramuscular (im), and subcutaneous (sc) injection, if not more effective. The in/or route was in fact as effective as ip injection, which is considered to be the most effective route in mice challenged iv with FLC. In contrast, administration of the same dose of IFN directly into the mouth appeared to be less effective than combined intranasal and oral administration, while introduction of IFN directly into the stomach of animals via a tube was considerably less effective.

EXAMPLE 4

Effect of Oromucosal Interferon on Expression of Cellular Proteins

IFN-α is known to induce the expression of a number of cellular proteins following binding of the protein to its cell surface receptor. These proteins are thought to provide a useful marker of IFN action.

We evaluated the effect of IFN-α administered via the in/or route on the expression of three IFN-induced proteins, MHC class I antigens, Ly 6A/E antigen and 2'–5'-oligoadenylate synthetase.

Treatment of DBA-2 mice (H-2K$^d$) with up to 20,000 IU of Mu IFN-α by the in/or route did not significantly increase H-$_2$-K$^d$ expression on peripheral blood lymphocytes, monocytes or granulocytes under conditions where as little as 20 IU of Mu IFN-α given ip markedly increased the expression of H-$_2$-K$^d$ antigens on both peripheral blood monocytes and granulocytes. Indeed, expression on monocytes was slightly suppressed.

Similarly, treatment of mice with up to 20,000 IU of IFN-α via the in/or route had no significant effect on the expression of Ly6 A/E antigens, the expression of which is markedly enhanced on the surface of a variety of lymphoid cells following parenteral treatment with type I IFN (Dumont et al; *J. Immunol.*, 1986 137: 201–210). Similar results were obtained with 200 or 20,000 IU of either Mu IFN-α or Hu IFN-α 1–8 via the in/or route.

Treatment of either Swiss or DBA/2 mice with as little as 20 IU of Mu IFN-α injected ip resulted in a marked increase in 2'-5'-oligoadenylate synthetase activity in both peripheral blood mononuclear cells and splenocytes. In contrast, in the same experiment treatment of mice with up to 20,000 IU of Mu IFN-α via the in/or route did not significantly increase the expression of 2'-5'-oligoadenylate synthetase activity. Furthermore, treatment with 200 or 20,000 IU of either Mu IFN-α or Hu IFN-α 1–8 by the in/or route had no significant effect on 2'-5'-oligoadenylate synthetase activity at any of the time points tested up to 10 days after the start of IFN treatment.

EXAMPLE 5

Bioavailability of Interferon Following Oromucosal Administration

In order to examine the bioavailability and pharmacokinetics of IFN, mice, which have the most favorable drug-blood volume ratio for such studies, were treated with a single high dose of recombinant IFN-α labeled to the highest specific radioactivity possible with $^{125}$I.

A pure preparation of $70 \times 10^6$ IU of Hu IFN-α 1–8 was taken up in 1.4 mls of PBS, and iodinated as described by Mogensen et al, (*Int. J. Cancer*, 1981 28: 575–582) using a modification of the chloramine-T method described by Hunter and Greenwood (*Nature*, 1962 194: 495–496).

The $^{125}$I-labeled Hu IFN-α 1–8 (lot no. CGP35269-1) exhibited a biological activity of $2 \times 10^7$ IU/ml when assayed on human WISH cells challenged with VSV and $1 \times 10^6$ IU/ml when assayed on mouse L929 cells challenged with VSV.

Six to seven week-old female Swiss mice were injected iv, ip, or treated in/or with $2 \times 10^7$ IU equivalent to $1 \times 10^6$ murine IU of $^{125}$I Hu IFN-α 1–8 ($1.0369 \times 10^7$ cpm/mouse). At the time points indicated, three mice per group were sacrificed, blood was collected, and the volume determined. Kidney, liver, lung, spleen, and stomach/esophagus were harvested, blotted, and weighed to a precision of $\pm 1.0$ μg. The radioactivity of each sample was determined individually using a gamma counter. Whole blood was then separated by centrifugation (800 g×10 min., 4° C.), the serum was harvested, counted, and frozen at −80° C. The serum was then assayed for IFN content using a standard bioassay on both human WISH cells and on mouse L929 cells as described above. The radioactive material present in the samples of serum was then isolated by affinity immunoprecipitation and analyzed by SDS-PAGE.

Very high levels of radioactivity ($>2 \times 10^6$ cpm/ml) were detected in the peripheral blood of animals 5 min. after injection of $1.0369 \times 10^7$ cpm/mouse of $^{125}$I-labeled Hu IFN-α 1–8 by iv bolus. The amount of radioactivity present in whole blood then declined progressively at 15 and 30 min. The levels of radioactivity detected in the peripheral blood of animals 5 min. after ip injection of $1.0369 \times 10^7$ cpm of $^{125}$I Hu IFN-α-1–8 were approximately twenty fold lower than the levels detected following an iv bolus. The levels of radioactivity then increased progressively at 15 and 30 min. post-injection. The levels of radioactivity detected in the blood of animals at 5, 10 or 15 min. after the in/or administration of $^{125}$I IFN-α 1–8 were significantly lower than those detected at a given time following ip injection of the same quantity of radiolabelled IFN. For all three routes of administration, higher levels of radioactivity were detected in serum than in whole blood following in/or administration of $^{125}$I-labeled IFN-α 1–8. The lower levels of radioactivity detected per ml of whole blood compared with the same volume of serum reflect the effectively larger volume of serum counted after removal of the cellular component of whole blood.

Samples of serum from all the mice in the study were assayed for the presence of biologically active IFN using a standard bioassay, as described above, and showed readily detectable levels of biologically active IFN in the serum of all the animals injected either iv or ip with $^{125}$I Hu IFN-α 1–8 at all the time points tested. In contrast, no biologically active IFN was detected in the serum of any of the animals at any of the time points tested following the in/or administration of IFN, in spite of the presence of relatively high levels of radioactivity in the serum of these animals.

In order to determine whether the radioactive material detected in the serum of animals treated with $^{125}$I Hu IFN-α 1–8 does indeed represent native IFN, the samples were immunoprecipitated with protein A-G Agarose, in order to precipitate immunoglobulins present in the samples, treated with an affinity-purified polyclonal anti-IFN-α antibody, and further immunoprecipitated. The samples were then subjected to SDS-polyacrylamide gel electrophoresis (SDS-PAGE) as described above.

SDS-PAGE analysis of the radioactive material in serum following iv or ip injection of $^{125}$I Hu IFN-α 1–8 revealed a single homogenous band migrating with an electrophoretic mobility identical to that of uninjected $^{125}$I Hu IFN-α 1–8. The apparent molecular weight of the material was estimated to be approximately 20000 Daltons, which corresponds exactly to the molecular weight of native Hu IFN-α 1–8. In contrast, none of the samples of serum from mice treated in/or with $^{125}$I IFN-α 1–8 contained any material with an apparent molecular weight similar to that of native IFN, even though an identical quantity of radioactive material was loaded on to each gel.

The tissue distribution of radiolabelled material revealed very high levels of radioactivity in the kidneys, high levels in the liver, lung, and spleen of animals 5 min. after the iv injection of $^{125}$I IFN-α 1–8. The level of radioactivity present in each of these four organs was then found to decrease progressively at 15 and 30 min. In contrast, the level of radioactivity in the stomach increased progressively at 15 and 30 min. to reach a level comparable to that present in the serum of animals 30 min. after an iv bolus.

Administration of $^{125}$I IFN-α 1–8 by ip injection resulted in peak levels of radioactivity in all the tissues examined within 15 min., followed by a decline at 30 min. Similarly, in/or administration of $^{125}$I Hu IFN-α 1–8 resulted in peak levels of radioactivity in all the tissues studied after 15 min. with some decline in the levels of radioactivity present at 30 min. The levels of radioactivity present in the stomach/esophagus were an order of magnitude greater than those detected in any other organ following the in/or administration of $^{125}$I-labeled IFN-α 1–8, and were markedly higher than the levels present in these tissues following parenteral administration of the same quantity of radiolabelled Hu IFN-α 1–8 by either the iv or ip routes.

EXAMPLE 6

Pharmacokinetics of Interferon Following Intranasal/Oral Administration

For precise determination of the pharmacokinetics of Hu IFN-α 1–8, mice were treated iv, ip or in/or with $1.0369 \times 10^7$ cpm/mouse of $^{125}$I-labeled Hu IFN-α 1–8, and the levels of radioactivity present in both whole blood and serum were determined at a series of time points over a 24 hour period.

The pharmacokinetic profile of $^{125}$I-labeled Hu IFN-α 1–8 present in the blood of mice after an iv bolus closely followed a logarithmic clearance curve. This agreed with results of a previous study carried out in mice using a closely related molecule, recombinant human I A/D (Bg1) (Bohoslawed et al; *J. IFN Res.,* 1986 6: 207–213). The amount of bioavailable material, calculated from the area under the curve of concentration versus time, was also similar to that for human α A/D. A biphasic time-consuming clearance curve was observed following an iv bolus of $^{125}$I IFN-α 1–8, which is characteristic of substances which are cleared through the kidneys, in agreement with the results of Example 4. The pharmacokinetics of $^{125}$I-labeled IFN-α 1–8 following ip injection closely resembled those previously reported for IFNs administered im.

Readily detectable levels of biologically active IFN were present in the serum of all the animals following either an iv bolus or ip injection of $^{125}$I-labeled IFN-α 1–8.

The Friend erythroleukaemia model constitutes a very severe preclinical test of anti-tumor activity, since FLC are highly malignant and metastasize to both the liver and spleen when injected iv. Indeed, results obtained using this model were the basis for the adoption of parenteral injection of IFN-α for treatment of human cancers. Thus, in all the experiments carried out in this study all the untreated animals and animals treated with control preparations died within 10 to 11 days. Injection of only 4 or 5 FLC cells will kill a mouse if no treatment is given. In contrast some of the animals treated with murine IFN-α by the oromucosal route are still alive more than 100 days after inoculation of $10^5$ FLC, and may be considered to be cured.

Indeed, judging from previous work, IFN-α administered by the oromucosal route appears to be more effective than cyclophosphamide, 5-fluorouracil or methotrexate administered parenterally, which increase survival time by only a few days in animals injected with FLC (Gresser et al, *J. Natl. Cancer Inst.,* 1988 80: 126–131). Other drugs, such as cisplatin, vincristine, doxorubicin, bleomycin or etoposide are ineffective against this tumor (Gresser et al, *J. Natl. Cancer Inst.,* 1988 80: 126–131).

Similarly, IFN-α administered by the oromucosal route appears to be more effective against FLC than other cytokines such as IL-1β, IL-2 and TNF-α administered systemically, which exhibit very little activity in this model.

Previous work has shown that IFN administered parenterally is one of the most active anti-tumor drugs in this model and that IFN therapy is effective even when initiated after tumor metastases are already present in the liver (Gresser et al., *Intl. J. Cancer,* 1987 39: 789–792). The present results show that IFN administration by the oromucosal route is equally, or even more, effective.

Daily injections of IFN-α given together with a single dose of cyclophosphamide markedly increased the survival of lymphoma-bearing AKR mice compared to animals treated with either agent alone, when therapy was started after diagnosis of the lymphoma (Gresser et al, *Eur. J. Cancer,* 1978 14: 97–99). Successful combination therapy using IFN-α/β and BCNU, cis-DDP (cisplatin), methotrexate, adriamycin, and α-difluoromethyl ornithine has also been reported in various pre-clinical animal tumor models. Combination therapy with 5-fluorouracil (5-FU) and IFN has also been reported to be of benefit in the treatment of metastatic colon cancer in man (Ernstoff et al, *Journal of Clinical Oncology,* 1989 7: 1764–1765). There are, however, other studies which have reported a decreased anti-tumor activity when IFN therapy was combined with the use of cyclophosphamide (Marquet et al, *Int. J. Cancer,* 1983 31: 223–226; Lee et al, *Biochem. Phannacol.,* 1984 33: 4339–3443), adriamycin (Blackwill et al, *Cancer Res.,* 1984 44: 904–908), or 5-FU (Marquet et al, 1985 109: 156–158), i.e. precisely the same drugs which have been shown to exert a beneficial effect when used in combination with parenteral IFN therapy. Combinations between IFN and other chemotherapy agents can readily be tested using methods described herein.

Combined interleukin-1 (IL-1) and IFN-α/β therapy results in a synergistic anti-tumor effect in mice injected with FLC (Belardelli et al, *Int. J. Cancer,* 1991 49: 274–278). The same treatment also exerts a marked anti-tumor effect against a metastatic variant (p11-R-Eb) of the Eb lymphoma, against which either agent alone is ineffective (Gabriele et al, *Invasion Metastasis,* 1993 13: 147–162). Of all the cytokines tested, IL-1 was found to be the most effective when combined with parenteral type I IFN therapy.

Combination therapy with the angiogenesis inhibitor AGM-1470 [(Chloroacetyl)-carbamic acid (3R-(3α, 4α (2R*, 3R*), 5β, 6β))-5-methoxy-4-(2-methyl-3-(3-methoxy-2-butenyl)oxiranyl)-1-oxaspiro(2.5)oct-6-yl ester] given together with IFN-α/β resulted in a markedly increased anti-tumor effect compared to that observed with either agent alone (Brem et al, *J. Pediatric Surgery,* 1993 28: 1253–1257).

It has been shown that hyperthermia enhances the anti-tumor action of IFN-α/β against the Lewis lung carcinoma (Yerushalmi et al, *Proc. Soc. Exp. Biol. Med.,* 1982 169: 413–415). Arginine butyrate has also been shown to potentiate the anti-tumor action of IFN-α (Chany and Cerutti, *Int. J. Cancer,* 1982 30: 489–493).

Comparison of the degree of protection obtained when a given type and dose of IFN was administered by the oromucosal route compared to the results obtained following systemic administration (ip injection) showed that parenteral administration of IFN was in some cases marginally more effective, and in other cases no more effective, than oromucosal administration.

The results of the biomarker pilot study show quite clearly that none of the three biomarkers tested (MHC class I antigen, Ly6 A/E antigen, and 2'-5'-oligoadenylate synthetase activity) adequately reflects the very marked antitumoral activity exhibited by IFN-α administered by the oromucosal route.

The contrast between the very marked increase in the expression of all three IFN-induced proteins observed in all the experiments undertaken following the ip injection of as little as 20 IU of IFN-α and the absence of any detectable effect following the administration of up to 20,000 IU of IFN-α via the oromucosal route is striking.

Although we cannot exclude the possibility that an effect on one or other of the biomarkers would have been observed at an earlier or intermediate time point, this seems to be unlikely, as IFN acts on the transcription of the genes coding for these proteins and thus one would not expect to see an effect on any of these biomarkers until a number of hours after IFN treatment.

Again, although we cannot exclude the possibility that a systemic effect on one of the other numerous IFN-induced proteins would have been observed following treatment with IFN-α by the oromucosal route, this seems unlikely, as this would imply differential regulation of the expression of certain IFN-induced genes. It is entirely possible, however, that an effect on an IFN biomarker may be observed locally, for example, in nasal lymphocytes following administration of IFN-α via the oromucosal route.

In keeping with the absence of a detectable effect on the biomarkers studied, no consistent effect was observed on any of the hematological or blood chemistry parameters monitored during oromucosal IFN therapy, even in animals treated with up to 20,000 IU of IFN-α.

Readily detectable levels of radiolabelled material were found in both whole blood and serum of animals following oromucosal administration of $^{125}$I-labeled IFN-α 1–8. These results contrast with the results of previous studies, which failed to detect IFN in the serum of animals even after the oral administration of large quantities of unlabelled IFN. However, the radioactive material detected in both whole blood and serum following oromucosal administration was biologically inactive. Furthermore, the results of SDS-PAGE analysis showed that this material was of low molecular weight, and most probably reflected the absorption of degradation products following digestion of IFN in the stomach and small intestine. Analysis of the tissue distribution of radiolabelled material following oromucosal administration revealed markedly higher levels of radioactivity in the stomach than in any of the other organs tested. Our results show quite clearly that even though biologically active IFN was not absorbed following oromucosal administration, this treatment does nevertheless exert a statistically significant antitumor activity in vivo.

Without wishing to be bound by any proposed mechanism for the observed beneficial effect, our results suggest that oromucosally administered IFN exerts its effects against tumor cells via a presently undefined novel mechanism, which does not involve a direct action of exogenously administered IFN, or the induction of endogenous IFN. This is supported by the absence of detectable levels of circulatory IFN or of the three biomarkers tested. It appears that this mechanism may act at least partly by stimulation of the abundant lymphoid tissue surrounding the nasopharyngeal and oral cavities. Since we have shown that oromucosal IFN is at least comparable in efficacy to systemically administered IFN, our results provide strong support for administration of IFN by the oromucosal route in the treatment of neoplastic disease. This could have important implications for the clinical use of IFN.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

What is claimed is:

1. A method for treating a neoplastic condition in a mammal which method comprises administering to the mammal a therapeutically effective amount of an interferon via oromucosal contact, said amount being from about 1500 IU to about 20×10$^6$ IU for a 70 kg man per day, said amount being less than an amount which induces a pathological response in the mammal when administered parenterally.

2. A method of claim 1 in which the effective dose of interferon is administered in a single dose.

3. A method of claim 1 in which the effective dose of interferon is administered in a plurality of smaller doses over a period of time sufficient to elicit a therapeutic response equivalent to that of a single dose.

4. A method of claim 1 in which the dose of interferon is administered continuously over a period of time sufficient to elicit a therapeutic response equivalent to that of a single dose.

5. A method of claim 1 in which the total dose of interferon is from about 5000 IU to about 20×10$^6$ IU of interferon per day.

6. A method of claim 1 in which the dose of interferon is from about 1×10$^4$ IU to about 20×10$^6$ IU of interferon per day.

7. A method of claim 1 in which the dose of interferon is from about from about 1×10$^4$ IU to about 1×10$^6$ IU of interferon per day.

8. A method of claim 1 further comprising conjunctive radiation or chemotherapy.

9. A method of claim 1 further comprising the administration of other cytokines or interferon inducers.

10. A method of claim 1 wherein the interferon comprises a Type I interferon.

11. A method of claim 10 wherein the interferon is selected from the group consisting of IFN-α, IFN-β, IFN-ω, consensus IFN, and mixtures thereof.

12. A method of claim 11 wherein the IFN-α comprises recombinant IFN-α.

13. A method of claim 1 wherein the interferon comprises a Type II interferon.

14. A method of claim 13 wherein the Type II interferon comprises γ-IFN.

15. A method of claim 1 wherein the neoplastic condition is of non-viral etiology.

16. A method for treating multiple myeloma, hairy cell leukemia, chronic myelogenous leukemia, low grade lymphoma, cutaneous T-cell lymphoma, carcinoid tumors, kidney tumors, carcinomas including renal cell carcinoma, hepatic cellular carcinoma, hematological malignancies, colorectal cancer, glioblastoma, lung cancer, colon cancer, malignant melanoma, and brain tumors including malignant brain tumors in a mammal which method comprises administering to the mammal a therapeutically effective amount of an interferon via oromucosal contact, said amount being from about 1500 IU to about 20×10$^6$ IU per day, said amount being less than an amount which induces a pathological response in the mammal when administered parenterally.

* * * * *